(12) United States Patent
Mane et al.

(10) Patent No.: US 6,943,272 B2
(45) Date of Patent: Sep. 13, 2005

(54) NORBORNANE AND NORBORNENE DERIVATIVES, USE THEREOF AND PERFUMED PRODUCTS CONTAINING SAME

(75) Inventors: Jean Mane, Grasse (FR); Jean-Jacques Chanot, Mougins (FR); Fabrice Le Borgne, Roquefort-les-Pins (FR); Martin Schroeder, Grasse (FR)

(73) Assignee: V. Mane Fils, Bar-sur-Loup (FR)

( * ) Notice: Subject to any disclaimer, the term of this patent is extended or adjusted under 35 U.S.C. 154(b) by 0 days.

(21) Appl. No.: 10/492,859

(22) PCT Filed: Oct. 23, 2002

(86) PCT No.: PCT/FR02/03629

§ 371 (c)(1),
(2), (4) Date: Apr. 16, 2004

(87) PCT Pub. No.: WO03/035595

PCT Pub. Date: May 1, 2003

(65) Prior Publication Data

US 2005/0004378 A1 Jan. 6, 2005

(30) Foreign Application Priority Data

Oct. 23, 2001 (FR) ............................................. 01 13663

(51) Int. Cl.[7] ........................ C07C 41/01; C07C 43/115; C07C 43/15
(52) U.S. Cl. ........................ 568/665; 568/667; 568/670; 568/55; 568/58; 568/338; 568/339; 568/343; 568/374; 568/376; 568/377; 568/379; 568/821; 549/430; 560/256; 562/400; 562/510; 564/454; 512/12; 512/14
(58) Field of Search .................................. 568/665, 667, 568/670, 55, 58, 338, 339, 343, 374, 376, 377, 379, 821; 549/430; 562/400, 510; 564/454; 512/12, 14; 510/119, 131, 276; 424/70.1, 76.1; 560/256

(56) References Cited

FOREIGN PATENT DOCUMENTS

WO PCT/FR02/03629 10/2002

OTHER PUBLICATIONS

Buchbauer et al., J. Soc. Cosmet. Chem., May 1978, vol. 29, pp. 307–322..*

International Preliminary Examination Report, Jun. 3, 2003.

* cited by examiner

*Primary Examiner*—Rosalynd Keys
(74) *Attorney, Agent, or Firm*—Alice O. Martin; Barnes & Thornburg, LLP

(57) ABSTRACT

The invention concerns a novel compounds of formula (I), wherein the dotted line bond is present or not, and wherein $R_1$ represents: when the dotted line bond is present —$CHCH_3OH$ or —$CHCH_3OCOR$ or —$CHCH_3XCH_2CHOHR'$ or —$CHCH_3OCHR'CH_2OH$ or formula (II) when the dotted line bond is absent —$CHCH_3OH$ or —$CHCH_3OCOR$ or —$COCH_3$ or formula (II) or —$CHCH_3XCH_2CHOHR'$ or —$CH_2CH_2XCH_2CHOHR'$ or —$CHCH_3OCHR'CH_2OH$ or —$CHCHCOR'$ or —$CH_2CH_2CHR'OH$ or —$CH_2CH_2CHR'OCOR$ or $CHCHCHOHR'$ or —$CHCHCHR'OCOR$, wherein R represents H, Me, Et, Pr, isoPr, But, isoBut, $CH_3CH_2)_4$, $(CH_3)_2CHCH_2$, $CH_2CH$, $(CH3)_2CCH$, and R' represents H, Me or Et, and X represents O, N or S, and their preparation method. Because of their fragrance, said compounds are highly interesting for the perfume industry, for cosmetic and care products.

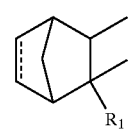

(I)

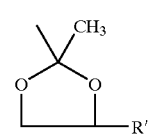

(II)

12 Claims, No Drawings

NORBORNANE AND NORBORNENE DERIVATIVES, USE THEREOF AND PERFUMED PRODUCTS CONTAINING SAME

FIELD OF THE INVENTION

The present invention relates to novel norbornane or norbornene derivatives, which have a particular fragrance, especially a woody or amber odor, and to their use in the fragrance industry.

The term "fragrance industry" is used herein to denote not only perfumery in the strict sense of the word, but also other fields in which the odor of products is important, in particular cosmetics, cleaning products, air fresheners and the like.

BACKGROUND OF THE INVENTION

It has been sought for a long time to synthesize novel compounds with a given odor, for use in the fragrance industry. The inspirational basis has often been natural products, on which attempts have been made to separate out the molecule(s) with olfactory properties.

In particular, the odor of sandalwood oil has been the subject of much research. After having identified the two main molecules that give natural sandalwood oil its odor, namely α-santalol and β-santalol, attempts were made to discover other molecules that might contribute to this odor. Attempts were also made to synthesize molecules that can reproduce this odor. The history of this research is reviewed in the article "*The Chemistry of Sandalwood Fragrance—a Review of the Last Ten Years*" by E.-J. Brunke et al., 15th Journées Int. Huiles Essentielles, Dignes-les-Bains, France, 5–7 Sep. 1996.

U.S. Pat. No. 4,229,600 relates to particular norbornane or norbornene derivatives that have the odor of sandalwood oil.

In the search for novel molecules, inspiration was drawn, of course, from the structures of known molecules, but experience has shown that the result was often random. Mention may be made, for example, of the article mentioned above in which is described a structure/odor correlation model, immediately followed by a counterexample, a molecule synthesized according to this model, but which does not have the expected odor. This same article cites a certain number of molecules of similar structure but whose olfactory properties are different, some having an odor, and others not.

Thus, there is no systematic method for designing a molecule as a function of the desired odor, from known molecules, via the implementation of logical and reproducible steps.

SUMMARY OF THE INVENTION

After extensive research, the Applicants have discovered a novel family of odoriferous molecules.

This family is represented by the following formula:

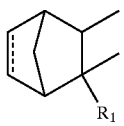

(I)

in which the dotted bond is present or absent, and in which $R_1$ represents:

when the dotted bond is present
—CHCH$_3$OH or —CHCH$_3$OCOR or
—CHCH$_3$XCH$_2$CHOHR' or
—CHCH$_3$OCHR'CH$_2$OH or

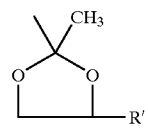

when the dotted bond is absent
—CHCH$_3$OH or —CHCH$_3$OCOR or —COCH$_3$ or

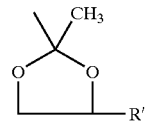

or —CHCH$_3$XCH$_2$CHOHR' or
—CH$_2$CH$_2$XCH$_2$CHOHR' or
—CHCH$_3$OCHR'CH$_2$OH or —CHCHCOR' or
—CH$_2$CH$_2$CHR'OH
or —CH$_2$CH$_2$CHR'OCOR or —CHCHCHOHR' or
—CHCHCHR'OCOR,
in which R represents H, Me, Et, Pr, isoPr, But, isoBut, CH$_3$(CH$_2$)$_4$, (CH$_3$)$_2$CHCH$_2$, CH$_2$CH or (CH$_3$)$_2$CCH, R' represents H, Me or Et, and X represents O, N or S.

DETAILED DESCRIPTION OF THE INVENTION

Each of the compounds of this family may be synthesized directly or indirectly from compound (c) below:

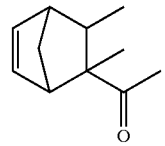

This compound, 1-(2,3-dimethylbicyclo[2,2,1]hept-5-en)-ethanone, which has already been described in the literature, and which is referred to in this patent application as Presantone, may be obtained, for example, by condensation of 3-methyl-3-penten-2-one (a) and cyclopentadiene (b), in a Diels-Alder reaction in aqueous phase, catalyzed with methylrhenium trioxide.

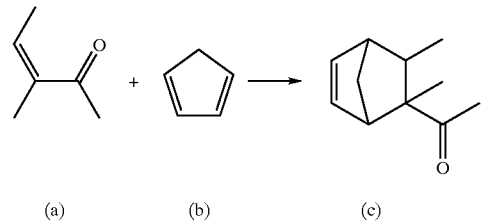

(a)  (b)  (c)

Needless to say, other reactions for preparing Presantone may be used, for example with other catalysts, or a particular solvent.

3-methyl-3-penten-2-one (a) is readily obtained, for example, by condensation of acetaldehyde or paraldehyde with methyl ethyl ketone. This product is commercially available and inexpensive.

Cyclopentadiene (b) may be obtained, for example, via several known methods for the depolymerization of dicyclopentadiene, which is produced by the petroleum industry.

Presantone may be the starting material or an intermediate in the synthesis of the compounds according to the invention. By way of nonlimiting example, a reaction scheme for the preparation of novel compounds according to the invention is given below.

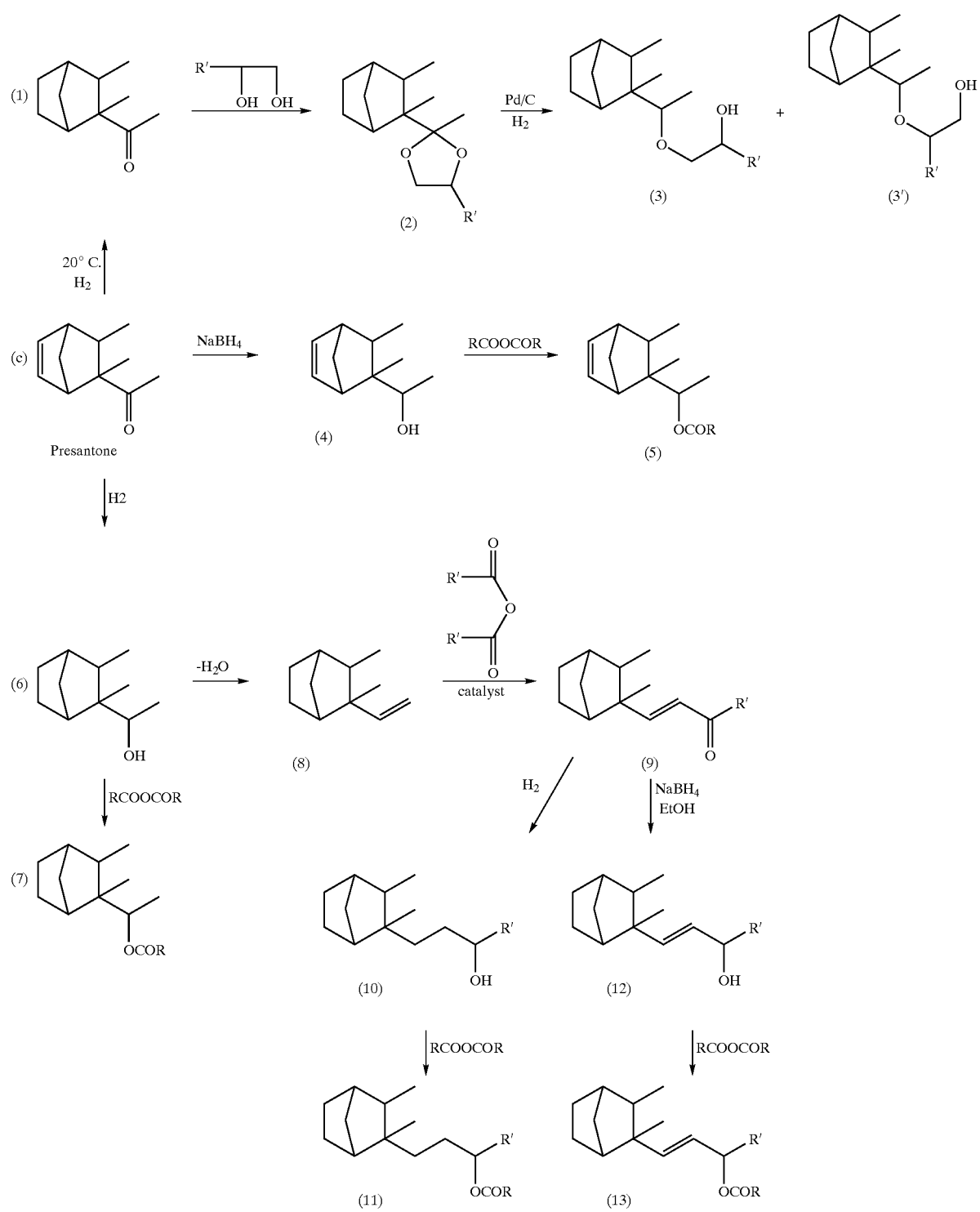

R = H, Me, Et, Pr, isoPr, But
isoBut, CH$_3$(CH$_2$)$_4$, (CH$_3$)$_2$CHCH$_2$,
CH$_2$CH or (CH$_3$)$_2$CCH
R' = H, Me or Et The abbreviations Me, Et, Pr, isoPr, But and isoBut have the usual meanings known to those skilled in the art, namely methyl, ethyl, propyl, isopropyl, butyl and isobutyl, respectively.

The hydrogenation of Presantone (c) at low temperature (between 20° C. and 50° C.) in the presence of Raney nickel, palladium-on-charcoal or other suitable catalysts gives the saturated ketone (1). This ketone has a strong resinous woody note, the originality of which is appreciated by fragrance formulators.

According to the invention, the acetal (2) of the ketone (1) with, for example, propylene glycol, obtained via the standard acetalization methods, is hydrogenated in the presence, for example, of pure palladium-on-charcoal or mixed palladium-on-charcoal to open the acetal into the alcohol ethers (3) and (3'), which are separable by chromatography. The operation is performed with or without a solvent. The process is preferably performed under 30 kg to 120 kg of hydrogen at temperatures of between 120° C. and 180° C. The alcohol ethers (3) and (3') obtained have a strong, woody, long-lasting odor, whence arises their great interest for the fragrance industry, cosmetics, soaps, cleaning products, detergents and other fragranced products. The acetal (2) is itself also a novel compound that is advantageous on account of its odor.

The reduction of Presantone (c) with sodium borohydride gives the unsaturated alcohol (4), a novel product that is also advantageous.

The standard methods of esterification, for example using the acid anhydrides, allow the esters (5) to be obtained, i.e. the formic, acetic, propionic, butyric, isobutyric, etc. esters especially, from the alcohol (4). These esters are all novel compounds that may be used in the fragrance industry for their originality in the woody notes.

The hydrogenation of Presantone (c) in the presence of Raney nickel, for example at temperatures of between 100° C. and 180° C. under 20 kg to 100 kg of hydrogen, gives the saturated alcohol (6), which is also an advantageous compound.

The esterification of this saturated alcohol (6) with acid anhydrides, for example, gives the saturated esters (7), R being a hydrogen, methyl, ethyl, propyl, isopropyl, butyl, isobutyl, $CH_3(CH_2)_4$, $(CH_3)_2CHCH_2$, $CH_2CH$ or $(CH_3)_2CCH$ radical. All these novel esters have odors that are advantageous for the fragrance industry, due to their original fruity woody nature.

A second route was found from the saturated alcohol (6). Via dehydration of this alcohol via well-known methods, the ethylenic hydrocarbon (8) is obtained.

Acylation, for example with acetic or propionic anhydride in the presence of boron trifluoride etherate or zinc chloride, gives the ethylenic ketones (9). Any other known acylation method may be used.

Reduction of the ethylenic ketones (9) with sodium borohydride in alcohol is a simple method for obtaining the ethylenic alcohols (12), which are novel compounds that are also very advantageous. The esters (13) of the alcohols (12), obtained via standard methods, for example using the acid anhydrides, develop milder but long-lasting woody notes which are also highly appreciated by fragrance formulators.

The total hydrogenation of the ethylenic ketones (9) via the standard methods gives the saturated alcohols (10), and their esterification via any usual method, for example using the acid anhydrides, gives the esters (11), R being a hydrogen, methyl, ethyl, propyl, isopropyl, butyl, isobutyl, $CH_3(CH_2)_4$, $(CH_3)_2CHCH_2$, $CH_2CH$ or $(CH_3)_2CCH$ radical. These compounds also have advantageous woody odors.

It is also possible to prepare compounds (14) and (14')—which are separable by chromatography—by opening ethylene, propylene or butylene oxide, to give ethylene glycol, propylene glycol or butylene glycol, respectively, with the alkoxide of compound (4):

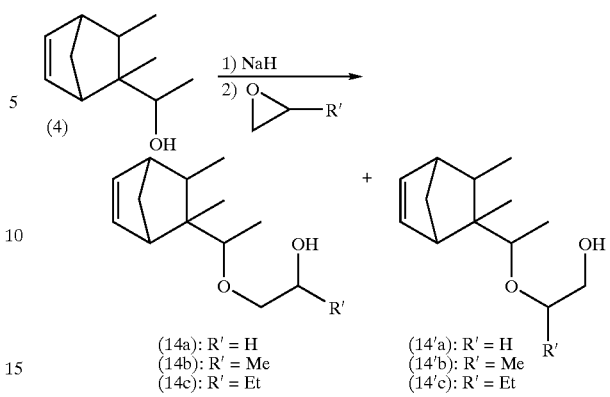

(14a): R' = H
(14b): R' = Me
(14c): R' = Et (14'a): R' = H
(14'b): R' = Me
(14'c): R' = Et

Another process for preparing compounds (3) and (3') from compound (6) may be mentioned. These compounds may be obtained from the alkoxide of compound (6) via the opening of ethylene, propylene or butylene oxide to give the corresponding glycol:

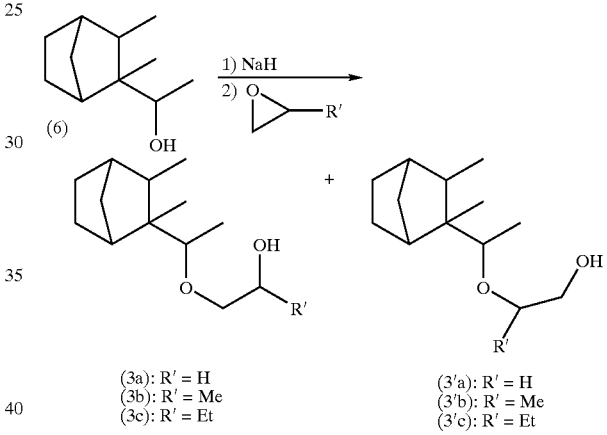

(3a): R' = H
(3b): R' = Me
(3c): R' = Et (3'a): R' = H
(3'b): R' = Me
(3'c): R' = Et

The invention also relates to another process for preparing compounds (3) and (3'), characterized in that the starting material or an intermediate is the novel compound of formula (2')

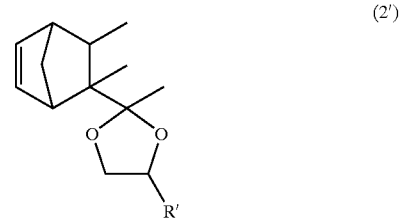

in which R' is H, Me or Et.

The acetal (2') may also be the starting material or the intermediate in the synthesis of the compounds of formulae (14) and (14').

The acetal (2') may be prepared, for example, directly by Diels-Alder reaction catalyzed with $FeCl_3$ between cyclopentadiene and the acetal (d).

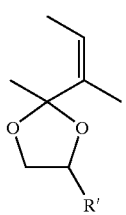

(d)

The acetal (d) (in which R′=CH₃) may be obtained by acetalization from the methyl-pentenone (a) and propylene glycol.

In one embodiment, the acetal (2′) allows the synthesis of compounds (3) and (3′), for example via a one-step hydrogenation catalyzed with palladium-on-charcoal.

The acetal (2′) also allows the synthesis of compounds (14) and (14′) via hydrogenation, for example with a hydride.

The invention also relates to other novel compounds, similar to compounds (3) and (14), in which the oxygen atom has been replaced with a sulfur or nitrogen atom. These are the compounds (15) to (18) below:

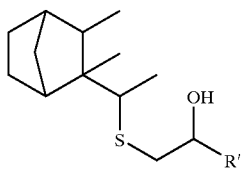
(15a): R′ = H
(15b): R′ = Me
(15c): R′ = Et

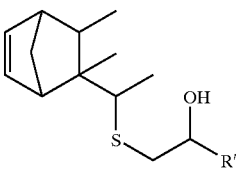
(17a): R′ = H
(17b): R′ = Me
(17c): R′ = Et

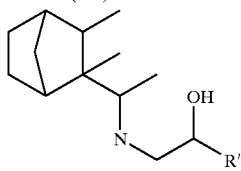
(16a): R′ = H
(16b): R′ = Me
(16c): R′ = Et

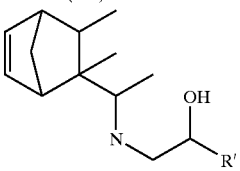
(18a): R′ = H
(18b): R′ = Me
(18c): R′ = Et

The sulfur compounds (15) [(15a), (15b) and (15c)] may be obtained from compound (1) according to the following process:

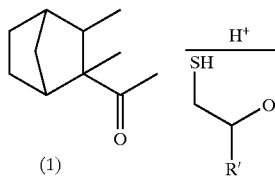

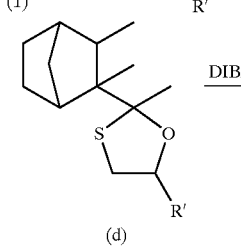
(d)
(15a): R′ = H
(15b): R′ = Me
(15c): R′ = Et

The oxathiolane (d) may be obtained via a standard acetalization method, and the acetal is then opened regiospecifically via methods described in the literature, for example with DIBAL in refluxing toluene.

The sulfur compounds (17) [(17a), (17b) and (17c)] may be obtained in the same manner as above, starting with Presantone (c).

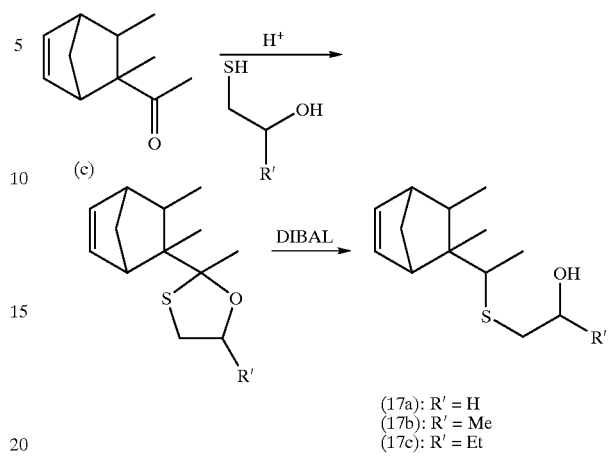
(17a): R′ = H
(17b): R′ = Me
(17c): R′ = Et

The nitrogen compounds (16) [(16a), (16b) and (16c)] and the sulfur compounds (15) [(15a), (15b) and (15c)], may be obtained from the alcohol (6), for example via mesylation, tosylation or halogenation, followed by nucleophilic substitution with the corresponding amino alcohol or thiol:

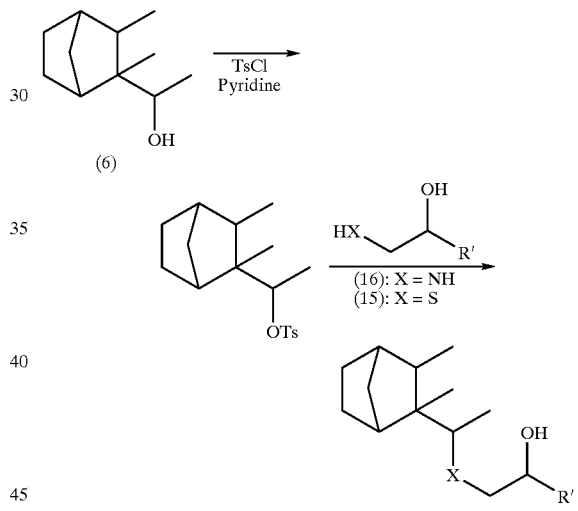
(16a) and (15a): R′ = H
(16b) and (15b): R′ = Me
(16c) and (15c): R′ = Et The amino alcohols (18) [(18a), (18b) and (18c)], and the thioethers (17) [(17a), (17b) and (17c)] may be obtained in the same manner as above, starting with the alcohol (4). The ethylenic hydrocarbon (8) also allows the synthesis of analogs containing a heteroatom in the side chain:

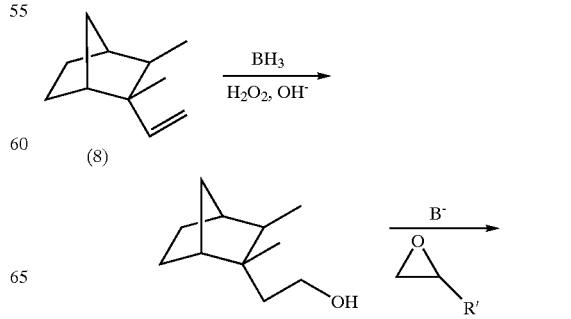

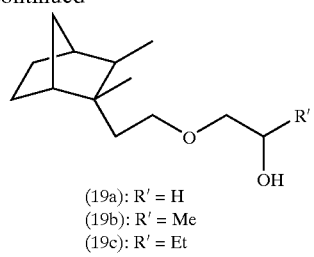

(19a): R' = H
(19b): R' = Me
(19c): R' = Et

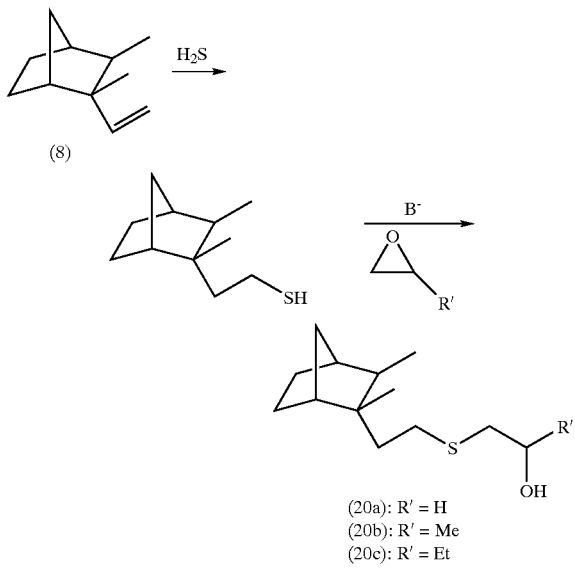

(20a): R' = H
(20b): R' = Me
(20c): R' = Et

The primary alcohol or thiol obtained by hydroboration of the double bond or addition of $H_2S$ is then condensed with ethylene, propylene or butylene oxide to give compounds (19) [a to c] and (20) [a to c]. Propylene oxide may optionally be replaced with the corresponding haloacetone to give, after reduction with $NaBH_4$, the expected alcohols (19b) and (20b).

The amino analogs (21) [a to c] may be obtained from the primary alcohol derived from hydrogenation via tosylation (or mesylation), followed by a substitution with the corresponding amino alcohol:

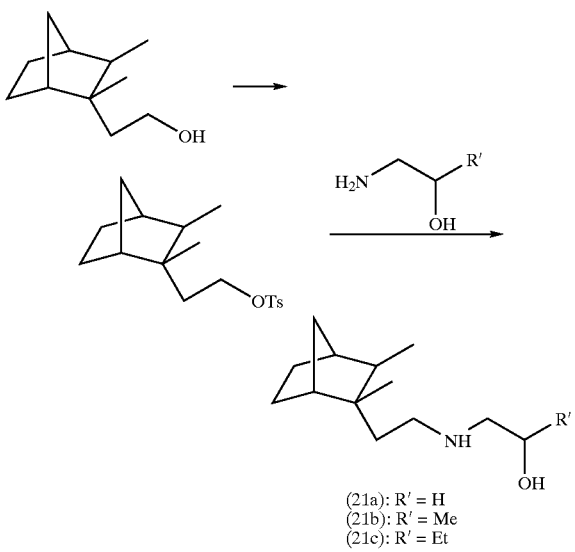

(21a): R' = H
(21b): R' = Me
(21c): R' = Et

A subject of the invention is the compounds represented by the general formula (I) in the form of a mixture of diastereoisomers in variable proportions, in particular the racemic mixtures.

Moreover, some of the diastereoisomers or enantiomers have olfactory properties that are as advantageous as the compounds obtained in the form of diastereoisomeric mixtures.

A subject of the invention is also the pure diastereoisomers or enantiomers of the novel compounds represented by the general formula (I), which may be separated by preparative gas chromatography. They may also be synthesized from optically active compounds, for example R or S propylene glycol and the alcohol (6) derived from the enantioselective reduction of Presantone (1–4), and purified by distillation.

A subject of the invention is also the processes for preparing the novel compounds.

Each of the novel compounds is advantageous on account of its odor, in particular its woody odor. Compound (3) with R'=Me is particularly advantageous. Moreover, the invention has an obvious economic advantage arising from the simplicity of the reactions used and the low cost of the starting materials used.

On account of their olfactory qualities, these various compounds thus find very varied use in the fragrance industry for the preparation of fragrancing bases and concentrates, perfumes and eaux de toilette, and also in the fragrancing of various consumer articles, such as soaps, shower gels or bath gels, shampoos and other hair hygiene products, cosmetic preparations, body deodorants, air fresheners, or alternatively textile detergents or softeners and cleaning products.

In these applications, the compounds according to the invention may be used alone or, as is more common in the fragrance industry, as a mixture with other fragrancing ingredients, solvents or adjuvants commonly used in the fragrancing industry, and which a person skilled in the art is capable of selecting as a function of the desired effect and of the nature of the product to be fragranced.

EXAMPLES

The concentrations in which these compounds and the isomeric mixtures thereof may be used to obtain the desired fragrancing effects vary within a very wide range of values (0.1% to 99%), it being well known that these values depend on the nature of the article to be fragranced, the desired odoriferous effect and the nature of the other ingredients in a given composition.

A subject of the invention is thus also the use of the novel compounds for the preparation of a fragrancing composition or a fragranced article, in the applications described above, in particular in perfumery, in cosmetics, for example for shampoos or soaps, and for cleaning products, such as softeners or detergents.

A subject of the invention is also the fragranced products comprising at least one compound according to the present invention, whether in the field of perfumery, cosmetics or cleaning.

The examples that follow further illustrate the various processes for manufacturing the novel compounds according to the invention and also their use and their advantage. These examples are given merely for the purpose of illustration and cannot be considered as limiting the invention.

Example 1

Diels-Alder Reaction (Presantone (c))

110 g of dry toluene are placed in a 500 ml round-bottomed flask with a magnetic stirrer, a thermometer, an addition funnel, and under nitrogen.

After cooling to 0° C., 4 g of aluminum chloride are added in a single portion, followed by addition, at about 10° C., of 88 g of 94% 3-methyl-3-penten-2-one (a) over 20 to 30 minutes, while cooling gently.

A solution of 66 g of cyclopentadiene (b) in 140 g of dry toluene is then added, at between 12° C. and 14° C., over 1 hour 10 minutes to 1 hour 20 minutes, while maintaining the temperature by cooling.

After separation of the phases by settling, the organic phase is washed with dilute hydrochloric acid (100 ml) and with a 5% carbonate solution. After concentrating the solvent under vacuum, the product is distilled off under 2 mm of vacuum (b.p.: 56–70° C./2 mm). 128 g of distillate are obtained. This product is taken up in toluene and treated with triethylamine and with a sodium carbonate solution. After washing and evaporating off the solvent under vacuum, the product is redistilled under a vacuum of 1 mm. 112 g of 1-(2,3-dimethylbicyclo[2,2,1]hept-5-en)ethanone are obtained (b.p.: 56–60° C./1 mm), yield: 76%.

The mixture is left stirring at 14–15° C. for a further 15 minutes and is then cooled to 0° C. and a solution of 20 g of 32% hydrochloric acid in 100 g of water is then added rapidly while allowing the temperature to rise.

The vapor-phase chromatography analysis shows the presence of two main isomers (32% and 56%).

The analyses of the infrared and mass spectra correspond to the structures of the expected compounds.

Example 2

Saturated Ketone (1)

The hydrogenation of 50 g of the ethylene ketone (c) in the presence of 0.5 g of Raney nickel at room temperature, and at a low pressure of hydrogen (1 to 10 kg) absorbs the theoretical amount of hydrogen over about 2 hours.

After separating out the catalyst, the product is distilled under vacuum. The saturated ketone (1) is obtained virtually quantitatively.

The product distils at 54° C.–58° C. under 1 mm of vacuum. The vapor-phase chromatography analysis shows two main peaks and the infrared and mass spectra correspond to the structures of the expected compounds.

Example 3

Ethylenic Alcohol (4)

Via reduction of 40 g of Presantone (c) in 200 ml of 96% alcohol, by adding 6 g of sodium borohydride portionwise at 25° C. over 2 hours, followed by gradually bringing the temperature to 40° C. over 2 hours and maintaining the mixture at this temperature for a further 3 hours, the total reduction of the ketone function to an alcohol is obtained.

After slow acidification, with 2% hydrochloric acid, extraction with toluene and washing, the product is concentrated under vacuum and then distilled.

36 g of ethylenic alcohol (4) are obtained, with a boiling point of 72–75° C. under 1 mm of vacuum, i.e. 90 mol% yield.

The vapor-phase chromatography analysis shows the presence of 3 main isomers that have very similar mass and infrared spectra.

Example 4

Ethylenic Esters (5)

By slowly bringing 10 g of ethylenic alcohol (4) in 10 g of acetic anhydride to 115–120° C. over 2 hours, the ethylenic acetate (5) is obtained.

The product obtained is concentrated under a vacuum of 30 mm to distil off the acid and the excess acetic anhydride through a 25 cm Vigreux column. The vacuum is slowly increased to 1 mm and the ethylenic acetate (5) is distilled off.

10 g of ethylenic acid (5) are obtained with a boiling point of 73–76° C. under 1 mm of vacuum.

The vapor-phase chromatography, MS and IR analyses correspond with the structures of the expected compounds.

The propionic, butyric and isobutyric esters of the ethylenic alcohol (4) are obtained by heating the alcohol (4) with the corresponding anhydrides, in the presence of a small amount of toluene, to maintain the reflux temperature at about 125–130° C.

The reflux time is increased to 2 hours to complete the esterification.

By distillation under vacuum, the acids and the anhydride esters are separated. By increasing the vacuum, the esters (5) are obtained.

Propionate of the ethylenic alcohol (5) with a boiling point of 80–83° C. under 1 mm of vacuum.

Butyrate of the ethylenic alcohol (5), with a boiling point of 88–91° C. under 1 mm of vacuum.

Isobutyrate of the ethylenic alcohol (5), with a boiling point of 85–88° C. under 1 mm of vacuum.

Example 5

Saturated Alcohol (6)

100 g of ethylenic ketone (c) are placed in an autoclave and are stirred and heated in the presence of 2 g of Raney nickel.

After flushing 3 times with 10 kg of hydrogen, the pressure is brought to 30 kg and the autoclave is heated to 150–160° C. with stirring.

The hydrogenation is performed under 60 kg of hydrogen until the pressure no longer falls (5 to 6 hours).

The crude saturated product (5) is distilled off under 1 mm of vacuum in an apparatus equipped with a 20 cm Vigreux column.

97 g of alcohol (5) are obtained, with a boiling point of 72–75° C. under 1 mm of vacuum.

The vapor-phase chromatography analysis shows that there are 4 main isomers, which have very similar mass and infrared spectra.

Example 6

Saturated Esters (7)

The saturated esters are obtained via the standard method used to make the unsaturated esters (Example 4), i.e. heating the saturated alcohol (6) in the presence of the corresponding acid anhydride.

Among the compounds obtained:

Acetate of the saturated alcohol (7), with a boiling point of 73–76° C. under 1 mm of vacuum, Propionate of the saturated alcohol (7), with a boiling point of 80–83° C. under 1 mm of vacuum, Butyrate of the saturated alcohol (7), with a boiling point of 88–91° C. under 1 mm of vacuum, Isobutyrate of the saturated alcohol (5), with a boiling point of 85–88° C. under 1 mm of vacuum.

Example 7

Alcohol Ether (3)

7.1. Acetal (2)

The acetal of the saturated ketone (1) and of propylene glycol may be prepared by refluxing, using a 30 cm Vigreux column and a water separator, propylene glycol (50 g), the ketone (1) (80 g) dissolved in toluene (40 g) and p-toluenesulfonic acid (0.4 g) as acid catalyst. The water is removed azeotropically (refluxing for 18 to 20 hours).

The toluene may also be removed and the water eliminated by distilling it off under vacuum.

The reaction mixture is washed with 5% sodium carbonate solution and then with water to neutral pH.

Fractionation under a strong vacuum in apparatus equipped with a 50 cm Vigreux column allows the following to be obtained:

25 g of recovered ketone (1) to be recycled, with a boiling point of 54–58° C. under 1 mm of vacuum.

65 g of acetal (2), with a boiling point of 64–58° C. under 1 mm of vacuum, 10 g of intermediate fractions to be recycled.

7.2. Alcohol Ether (3)

50 g of acetal (2), 100 g of isopropanol and 0.5 g of palladium-on-charcoal are placed in a stirred autoclave.

After flushing with hydrogen, the autoclave is maintained at between 160 and 170° C. under 50–60 kg of hydrogen for 18 to 24 hours.

The reaction progress is monitored by vapor-phase chromatography and the reaction is stopped when the percentage of acetal (2) has fallen to 5–6%.

After separating out the catalyst, the product is distilled off under 1 mm of vacuum in an apparatus equipped with a 50 cm Vigreux column. 6 g of head fractions are obtained.

Boiling point 40–50° C., 16 g of ketone (1)+acetal (2), with a boiling point of 54–68° C. under 1 mm of vacuum, to be recycled, and 25 g of alcohol ether (3), with a boiling point of 85–92° C. under 1 mm of vacuum. The mass and infrared spectra correspond with the structures of the expected compounds.

Example 8

Ethylenic Ketone (9)

8.1. Dehydration of the Alcohol (6)

150 g of alcohol (6) and 100 g of boric acid are placed in a 500 ml round-bottomed flask.

The mixture is heated under 40 mm of vacuum to remove the water of boratization and is then brought to a temperature of 230–250° C. to dehydrate. After distilling off 70 to 80 g of ethylenic compound (8), the dehydration is continued by introducing the alcohol (6) gradually as the dehydration proceeds.

Starting with 1 kg of alcohol (6), 880 g of ethylenic compound (8) containing 7–10% of alcohol (5) are obtained.

By fractionation on a 30 cm Vigreux column, 800 g of ethylenic compound (8) are separated out and 70 g of alcohol (6) to be recycled are recovered.

8.2. Ethylenic Ketone (9)

120 g of ethylenic compound (8) and 120 g of acetic anhydride are placed in a 1 liter round-bottomed flask with magnetic stirring, and the mixture is heated to 70–75° C. 16 ml of boron trifluoride etherate are then introduced over 15 minutes at 75–80° C. The temperature and stirring are maintained for 3 hours at 80–82° C.

After cooling to about 60° C., the excess acetic anhydride is decomposed by adding, slowly at the start, 320 g of water while maintaining the temperature at about 60–65° C.

The organic phase is separated out and the aqueous phase is extracted with twice 60 ml of cyclohexane. The combined organic phases are washed with 10% sodium carbonate solution and then with water.

After concentrating the solvent under a gentle vacuum, the crude product (138 g) is fractionated in an apparatus with a 30 cm Vigreux column. Under 5 mm of vacuum, 80 g of starting material (8) to be recycled and 32 g of ethylenic ketone (9) with a boiling point of 75–88° C. under 1 mm of vacuum are recovered.

Example 9

Ethylenic Alcohol (13)

30 g of ethylenic ketone (9) and 75 g of 96° ethanol are placed in a 250 ml round-bottomed flask with magnetic stirring and a thermometer. While cooling slightly, to maintain 20–25° C., 3 g of sodium borohydride are added portionwise. After the introduction, the mixture is stirred for 6 hours at room temperature and is then gradually heated to 40° C. over 2 to 3 hours, and then maintained at 40–45° C. for 4 hours.

A large proportion of the alcohol is concentrated under a gentle vacuum. 30 g of water are added to the residue, followed by slow acidification, while maintaining the temperature at 20–25° C., with 16 g of concentrated hydrochloric acid diluted with 50 g of water. 30 ml of toluene are then added, followed by separation of the phases by settling. The organic phase is separated out and the aqueous phases are extracted with twice 20 ml of toluene. After combining the organic phases, they are washed twice with 80 ml of water. The toluene is then concentrated under vacuum and the residue (30 g) is distilled under a strong vacuum in an apparatus equipped with a 15 cm Vigreux column.

25 g of ethylenic acid (12) are thus obtained, with a boiling point of 85–92° C. under 1 mm of vacuum, along with 3 g of product to be recycled. The infrared and mass spectra correspond to the structures of the expected compounds.

Example 10

Ethylenic Acetate (13)

30 g of ethylenic alcohol (12) and 25 g of acetic anhydride are placed in a 100 ml round-bottomed flask equipped with a magnetic stirrer, a thermometer and a 20 cm Vigreux column.

The mixture is heated under a gentle vacuum, such that the bulk temperature is 115–120° C., for 2 hours. The vacuum is then increased to distil off the acetic acid/anhydride mixture. The final bulk temperature is 125–130° C.

Under 1 mm of vacuum, the acetate (14) with a boiling point of 80–88° C. under 1 mm of vacuum is then distilled off. 27 g of acetate (13) and 3 g of product to be recycled are obtained. The infrared and mass spectra correspond to the structures of the expected compounds.

Example 11

Saturated Alcohol (10)

30 g of ethylenic ketone (9) and 0.6 g of Raney nickel are placed in a stirred and heated autoclave. After flushing with hydrogen, the mixture is brought to 150–160° C. under 60 kg of hydrogen.

The reaction is complete after 12 hours. The catalyst is separated out and the product is distilled off under a strong vacuum. 27 g of saturated alcohol (11) are obtained, with a boiling point of 82–90° C. under 1 mm of vacuum.

Example 12

Saturated Acetate (12)

By performing the process as for the ethylenic acetate (13) on 25 g of saturated alcohol (10), 26 g of acetate (11), with a boiling point of 78–86° C. under 1 mm of vacuum, are obtained by distillation.

Example 13

Alcohol Ether (3) via the Acetal (2')

46.00 g of dichloromethane are placed under nitrogen in the receiving flask of a distillation apparatus on which is mounted a 30 cm Vigreux column, and the flask is cooled to 0° C. The oil bath of the distillation apparatus is heated to about 195° C. in order to obtain a temperature of 165° C. inside the three-necked flask. 13.80 g (0.45 mol) of dicyclopentadiene are introduced dropwise via the top of the column, the cyclopentadiene thus freshly depolymerized being recovered in the cooled solvent. 56.00 g of a solution of cyclopentadiene in dichloromethane, i.e. a potential of 10.00 g of cyclopentadiene (0.151 mol) are obtained over 4 hours. Yield: 72.5%. The solution is used directly in the following Diels-Alder reaction.

14.80 g (0.076 mol) of 80.0% 2,4-dimethyl-2-(1-methyl-propenyl)[1,3]dioxalane and 1.5 g of iron (III) chloride silica are introduced into the round-bottomed flask under nitrogen and at room temperature, and the mixture is cooled to 0° C. 56.00 g of the solution of cyclopentadiene in dichloromethane are added dropwise at this temperature over 10 minutes. The mixture is stirred for 2 hours at 0° C. and then for 15 hours while allowing the bulk temperature to return to room temperature. The catalyst is filtered off and the solvent is evaporated under reduced pressure (about 35 mmHg=4.67×10$^3$ Pa). 23.00 g of a pale yellow oil are obtained, and are transferred into a microdistillation apparatus with a 15 cm Vigreux column. 1.5 g (5.6 mmol) of 83% 2-(2,3-dimethylbicyclo[2.2.1]hept-5-en-2-yl)-2,4-dimethyl-[1,3]dioxalane (sum of the isomers) are obtained. Yield: 7.4%.

Example 14

Olfactory Evaluation

In a first stage, the olfactory characteristics of compound (3) when R' is methyl were evaluated by a panel at the same time as the olfactory characteristics of commercially available known compounds. The evaluation panel is composed of several professionals, who evaluate each compound qualitatively and quantitatively. The results of the evaluations are collated in the table below.

| | Odor: | | | | | | |
|---|---|---|---|---|---|---|---|
| | Woody | Cedar | Amber | Vet-iver | Iris | Camphor | Leather |
| Compound (3) | XXX | XX | XX | | | XX | |
| Iso E Super[1] | XXX | X | XXX | X | | | |
| Vertofix[2] | XXX | XX | | | XX | | X |
| Bois-ambrene[3] | XXX | | XX | | | | X |

[1]2-Acetyl-1,2,3,4,5,6,7,8-octahydro-2,3,8,8-tetra-methylnaphthalene (mixture of isomers); from: International Flavors & Fragrances, USA.
[2]4-Acetyl-1,1,6-trimethyl-6,8a-ethano-1,2,3,4,5,6,7,8,8a-octahydronaphthalene; from: International Flavors and Fragrances, USA.
[3](Ethoxymethyl)cyclododecane; from: Henkel.

These three reference products are very widely used in fragrancing compositions for soaps, detergents and softeners or shampoos. They are also very commonly used in alcohol-based perfumery.

It may be observed that compound (3) has a woody, cedar, amber and camphor nature.

In a second stage, the impact or the olfactory characteristics of compound (3) when it is applied to a support were evaluated.

Three different supports were used:
as a 10% solution in 96° alcohol,
in a standard softening base at 0.5%: evaluation on wet laundry and on dry laundry,
in a standard shampoo base at 0.5%: evaluation of the base coverage and diffusion in solution in hot water.

Two base fragrancing compositions were prepared by mixing the ingredients listed below. The tests were performed by adding 50 parts by weight of compound (3) to the base mixture.

COMPOSITION 1
Test in detergent (application at 0.5%)

| COMPONENTS | TEST 1 | TEST 2 |
|---|---|---|
| GERANIUM RECO VMF[1] | 20 | 20 |
| BENZYL ACETATE | 60 | 60 |
| DIMETHYLBENZYLCARBINYL ACETATE | 20 | 20 |
| PHENOXYALLYL ACETATE | 2 | 2 |
| PHENYLETHYL ALCOHOL | 100 | 100 |
| HEXYLCINNAMALDEHYDE | 200 | 200 |
| C12 LAURYLALDEHYDE | 2 | 2 |
| C12 MNA ALDEHYDE | 3 | 3 |
| GAMMA-UNDECALACTONE | 7 | 7 |
| CITRONELLOL | 30 | 30 |
| COUMARIN | 15 | 15 |
| DIHYDROFLORIFONNE[2] | 1 | 1 |
| DIHYDROMYRCENOL | 50 | 50 |
| VERDYL ACETATE[3] | 15 | 15 |
| MADAGASCAR CLOVE ESS. | 12 | 12 |
| LILIAL[4] | 70 | 70 |
| METHYLIONONE | 55 | 55 |
| PHENYL OXIDE | 25 | 25 |
| ROSE OXIDE | 3 | 3 |
| AMYL SALICYLATE | 95 | 95 |
| BENZYL SALICYLATE | 135 | 135 |
| TRIPLAL[5] | 4 | 4 |
| VERDOX[6] | 20 | 20 |
| OXYPHENYLON at 10% EDG | 6 | 6 |
| COMPOUND (3) | | 50 |
| TOTAL | 950 | 1000 |

[1]V. MANE FILS
[2]1-(2,6,6-trimethyl-3-cyclohexen-1-yl)-2-buten-1-one
[3]3a,4,5,6,7,7a-hexahydro-4,7-methano-1H-inden-5 (or 6)-ol acetate - from Givaudan (Switzerland)
[4]p-tert-butyl-alpha-methyl-hydrocinnamaldehyde - from Givaudan (Switzerland)
[5]2,4-dimethyl-3-cyclohexene-1-carbaldehyde - from IFF (International Flavors and Fragrances, United States)
[6]2-tert-butylcyclohexyl acetate - from IFF COMPOSITION 2
Test in fragrance (application at 7%)

| COMPONENTS | TEST 1 | TEST 2 |
|---|---|---|
| STYRAX RECO VMF[1] | 5 | 5 |
| ISOBORNYLCYCLOHEXANOL to 50% EDG | 90 | 90 |
| YLANG RECO[1] | 25 | 25 |
| BENZYL ACETATE | 80 | 80 |
| PHENYLETHYL ALCOHOL | 80 | 80 |
| ANISALDEHYDE | 10 | 10 |
| BACDANOL[2] | 20 | 20 |
| CITRONELLOL | 55 | 55 |
| COUMARIN | 35 | 35 |
| DIHYDROMYRCENOL | 20 | 20 |
| ETHYLVANILLIN | 7 | 7 |
| GALAXOLIDE[3] | 140 | 140 |
| GERANIOL | 80 | 80 |
| HELIOTROPINE | 10 | 10 |
| PURE IRISONE[4] | 25 | 25 |
| LILIAL | 45 | 45 |
| METHYLIONONE | 25 | 25 |
| BENZYL SALICYLATE | 80 | 80 |
| VANILLIN | 8 | 8 |
| VERTENEX[5] | 80 | 80 |

-continued

COMPOSITION 2
Test in fragrance (application at 7%)

| COMPONENTS | TEST 1 | TEST 2 |
|---|---|---|
| C10 CAPRYLALDEHYDE at 10% DPG | 10 | 10 |
| C12 LAURYLALDEHYDE at 10% DPG | 15 | 15 |
| INDOL at 10% DPG | 5 | 5 |
| COMPOUND (3) |  | 50 |
| TOTAL | 950 | 1000 |

(1)V. MANE FILS
(2)4-(2,2,3-trimethyl-3-cyclopentenyl)-2-ethyl-3-buten-1-ol - from IFF
(3)1,3,4,6,7,8-hexahydro-4,6,6,7,8,8-hexamethylcyclopenta-(g)-2-benzan - from IFF
(4)mixture of ionones
(5)4-tert-butylcyclohexyl acetate - from IFF In each case, the evaluations of the olfactory impact were performed at $t_0$, $t_{+48h}$ and $t_{+168h}$ to evaluate the head note, core note and background note.

In all cases, it is observed that compound (3) gives an advantageous head note and base coverage, with a rich and original woody, camphor nature.

Whether in alcoholic solution (composition 2) or in a softening composition (composition 1), the rich woody amber note is very perceptible after 48 hours of drying and gives an original touch that is both clean and cosmetic.

The loss of intensity over time appears to be fairly linear without any appreciable change in olfactory characteristic being noticeable.

The diffusion in hot water in shampoo produces a discreet but sophisticated and very pleasant woody nature.

The results of these evaluations show unequivocally that compound (3) has advantageous olfactory characteristics, which will find application in particular in cosmetics, perfumery and cleaning products.

What is claimed is:

1. A novel compound of formula:

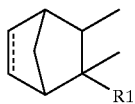

(I)

in which the dotted bond is present or absent, and in which R₁ represents:

when the dotted bond is present
—CHCH₃OH or —CHCH₃OCOR or
—CHCH₃XCH₂CHOHR' or
—CHCH₃OCHR'CH₂OH or

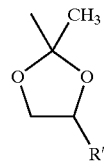

when the dotted bond is absent

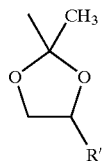

or —CHCH₃OH or —CHCH₃OCOR or —COCH₃ or
—CHCH₃XCH₂CHOHR' or
—CH₂CH₂XCH₂CHOHR' or
—CHCH₃OCHR'CH₂OH or —CH═CHCOR' or
—CH₂CH₂CHR'OH or —CH₂CH₂CHR'OCOR or
—CH═CHCHOHR' or —CH═CHCHR'OCOR, in which R represents H, Me, Et, Pr, isoPr, But, isoBut, CH₃(CH₂)₄, (CH₃)₂CHCH₂, CH₂═CH or (CH₃)₂C═CH, R' represents H, Me or Et, and X represents O, N or S.

2. The compound as claimed in claim 1, wherein the dotted bond is absent and R₁ is selected from the group consisting of —CHCH₃OCH₂CHOHCH₃ and —CHCH₃OCHR'CH₂OH.

3. The compound as claimed in claim 1, in the form of either a diastereoisomer or an enantiomer.

4. The compound as claimed in claim 1, in the form of a mixture of diastereoisomers.

5. The compound as claimed in claim 1, in the form of a racemic mixture.

6. A fragrancing ingredient for the preparation of either a fragrancing composition or fragranced article, said ingredient consisting of a compound of claim 1.

7. A product selected from the group consisting of fragranced products, perfumes, eau de toilette, cosmetic products, soaps, shower gels, bath gels, shampoos, hair hygiene products, cleaning products, detergent products, softening products, body deodorizers, and air fresheners, wherein said product comprises a compound as claimed in claim 1.

8. A process for preparing a compound as claimed in claim 1 comprising:

(a) hydrogenating or reducing an unsaturated ketone of formula

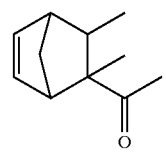

(c)

(b) reacting the compound resulting from (a) with a compound of formula R'CHOHCH₂OH or R'CHOHCH₂NH₂ or R'CHOHCH₂SH or RCOO-COR

wherein R' represents H, Me or Et, and R represents H, Me, Et, Pr, isoPr, But, isoBut, CH₃(CH₂)₄, (CH₃)₂CHCH₂, CH₂═CH or (CH₃)₂C═CH, or (b') dehydrating compound resulting from (a), reacting with R'COOCOR' wherein R' is as defined above, (c) optionally hydrogenating or reducing the compound resulting from (b) or (b')

(d) optionally reacting the compound resulting from (b') and (c) with RCOOCOR wherein R is as defined above.

9. A process according to claim 8 for preparing a compound as claimed in claim 1 comprising:

(a) hydrogenating an unsaturated ketone of formula

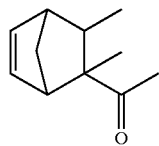

(c)

(b) reacting the compound resulting from (a) with a compound of formula R'CHOHCH$_2$OH wherein R' represents H, Me or Et, and (c) hydrogenating the resulting acetal of formula

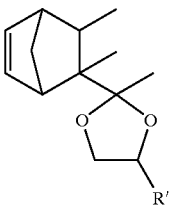

(2')

wherein R' represents H, Me or Et, to open said acetal.

10. A process according to claim 8 for preparing a compound as claimed in claim 1 wherein an unsaturated ketone of formula

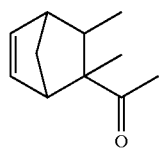

(c)

is prepared by reacting 3-methyl-3-penten-2-one with cyclopentadiene.

11. A process for preparing a compound as claimed in claim 1 in which R1 is selected from the group consisting of —CHCH$_3$OCH$_2$CHOHR' and —CHCH$_3$OCHR'CH$_2$OH wherein R' is H, Me or Et comprising hydrogenating or reducing an acetal of formula

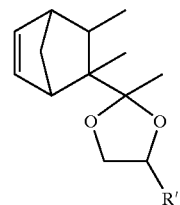

(2')

wherein R' represents H, Me or Et.

12. A process according to claim 11 for preparing a compound as claimed in claim 1 wherein an acetal of formula

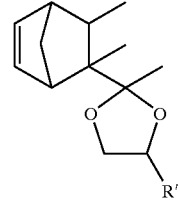

(2')

wherein R' represents H, Me or Et, is prepared by reacting cyclopentadiene with an acetal of formula

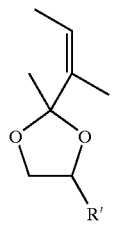

(d)

(d) wherein R' is as defined above.

* * * * *